United States Patent
Lita et al.

(10) Patent No.: US 8,370,352 B2
(45) Date of Patent: Feb. 5, 2013

(54) CONTEXTUAL SEARCHING OF ELECTRONIC RECORDS AND VISUAL RULE CONSTRUCTION

(75) Inventors: Lucian Vlad Lita, San Jose, CA (US); Maleeha Qazi, King of Prussia, PA (US); Radu Stefan Niculescu, Malvern, PA (US); Gilberto Augusto Matos, Plainsboro, NJ (US)

(73) Assignees: Siemens Medical Solutions USA, Inc., Malvern, PA (US); Siemens Corporation, Iselin, NJ (US)

( * ) Notice: Subject to any disclaimer, the term of this patent is extended or adjusted under 35 U.S.C. 154(b) by 577 days.

(21) Appl. No.: 12/251,636

(22) Filed: Oct. 15, 2008

(65) Prior Publication Data

US 2009/0106238 A1 Apr. 23, 2009

Related U.S. Application Data

(60) Provisional application No. 60/980,857, filed on Oct. 18, 2007, provisional application No. 61/076,783, filed on Jun. 30, 2008.

(51) Int. Cl.
*G06F 17/30* (2006.01)
(52) U.S. Cl. ........ 707/736; 707/708; 707/727; 707/728; 707/731; 704/4; 704/9; 705/1.1; 705/2
(58) Field of Classification Search .................. 707/708, 707/727, 728, 731, 736, 759, 999.005; 704/4–7, 704/9; 705/1.1, 2
See application file for complete search history.

(56) References Cited

U.S. PATENT DOCUMENTS

| | | | |
|---|---|---|---|
| 2002/0087510 A1* | 7/2002 | Weinberg et al. | 707/1 |
| 2003/0052788 A1* | 3/2003 | Kwong-Tai Chung | 340/573.1 |
| 2003/0217052 A1* | 11/2003 | Rubenczyk et al. | 707/3 |
| 2004/0049490 A1* | 3/2004 | Milov | 707/1 |
| 2004/0243545 A1* | 12/2004 | Boone et al. | 707/2 |
| 2005/0086049 A1* | 4/2005 | Bennett | 704/4 |
| 2005/0160082 A1* | 7/2005 | Dawson | 707/3 |
| 2006/0010011 A1* | 1/2006 | Ullom et al. | 705/2 |
| 2006/0149726 A1* | 7/2006 | Ziegert et al. | 707/5 |
| 2006/0200761 A1* | 9/2006 | Judd et al. | 715/517 |
| 2007/0061384 A1* | 3/2007 | Harrington et al. | 707/203 |
| 2007/0156677 A1* | 7/2007 | Szabo | 707/5 |
| 2007/0214030 A1* | 9/2007 | Shear et al. | 705/8 |
| 2007/0294289 A1* | 12/2007 | Farrell | 707/103 R |
| 2008/0091655 A1* | 4/2008 | Gokhale et al. | 707/3 |
| 2008/0208633 A1* | 8/2008 | Navani | 705/3 |
| 2008/0306926 A1* | 12/2008 | Friedlander et al. | 707/4 |

* cited by examiner

*Primary Examiner* — Dennis Truong
(74) *Attorney, Agent, or Firm* — Joshua Ryan

(57) ABSTRACT

A web-based system for visual construction of logical rules includes a server, a network, and client operatively connected to the server via the network. The server includes a database and a search engine. The client includes a web-based visual rule building application including selectable windows for displaying and visually editing terms, logical operators, logical rules for storage in the database. The logical rules are generated by visually selecting at least one of the terms and logical operators from the windows. The server may further include a search engine configured to perform at least one of a direct search or a contextual search for an entered query string in records stored in the database and the client may include a visual interface for displaying results of the searches. The search results generated by the search engine may be stored as terms in the database for subsequent rule generation.

19 Claims, 13 Drawing Sheets

CONTEXTUAL SEARCHING OF ELECTRONIC RECORDS AND VISUAL RULE CONSTRUCTION

CROSS-REFERENCE TO RELATED APPLICATIONS

This application claims priority to U.S. Provisional Application No. 60/980,857, filed on Oct. 18, 2007 and U.S. Provisional Application No. 61/076,783, filed on Jun. 30, 2008, the disclosures of which are incorporated by reference herein.

BACKGROUND OF THE INVENTION

1. Technical Field

The present disclosure relates to the field of text-based searching of electronic records and rule building, and more particularly to contextual searching of electronic records and visual rule construction.

2. Discussion of Related Art

The art of medical record keeping has developed over centuries of medical practice to provide an accurate account of a patient's medical history. Record keeping in medical practice was developed to help physicians, and other healthcare providers, track and link individual "occurrences" between a patient and a healthcare provider. Each physician/patient encounter may result in a record including notes on the purpose of the visit, the results of physician's examination of the patient, and a record of any drugs prescribed by the physician.

In addition to medical records, financial and legal records are becoming increasingly available in electronic format. Due to the high volume of data, it can be difficult to understand individual records in the context of a larger dataset (e.g., a patient record database of a medical institution). While conventional techniques for retrieving information from electronic records can find relevant documents, they do not provide statistical support for making decisions as to which portions of the documents are relevant. Further, the conventional techniques are not query driven and can not provide contextual information including statistics for user-driven requests. While conventional data mining platforms can extract data automatically from multiple records based on manually constructed logical rules, the logical rules can be complex and difficult to visualize.

Thus, there is a need for systems and methods to perform contextual searching of electronic records and a visual rule builder, which can enable a user to construct rules in a more intuitive manner.

SUMMARY OF THE INVENTION

An exemplary embodiment of the present invention includes a system for searching electronic records and displaying relevant data based on the search. The system includes a searching unit and a visual interface. The searching unit includes at least one of a direct searching unit or a context searching unit. The direct searching unit is configured to search for specific text in records. The direct searching unit may retrieve one or more documents or parts of a document (e.g., a paragraph, or sentence) based on an entered query string. The context searching unit is configured to search for text in the electronic records that are within a context of the entered query string. The visual interface is configured to display results of the searches. A context includes text that precedes or follows the entered query string in the electronic record that influences the meaning of the entered query string.

The system may include a statistical analyzer that is configured to analyze the search results and provide search statistics. The statistics may include frequency of occurrence of the search result, document type distributions, institutional distributions, etc.

An exemplary embodiment of the present invention includes a system configured to enable graphical building of logical rules. The logical rules may be used to search and/or extract data from electronic records that satisfy the rules. The system includes a visual interface for building the logical rules. The interface comprises a selectable window for displaying at least one of the logical rules. The logical rules are added to the window by selecting at least one of a plurality of logical operators and at least one of a plurality of terms. Each of the rules is represented by a tree in the window and the tree comprises at least one of the logical operators as a node of the tree and at least one of the lexicons as a leaf of the tree.

An exemplary embodiment of the present invention includes a web-based system for visual construction of logical rules. The system includes a server, a network, and client operatively connected to the server via the network. The server includes a database and a search engine. The client includes a web-based visual rule building application including selectable windows for displaying and visually editing terms, logical operators, and logical rules for storage in the database. The logical rules are generated by visually selecting at least one of the terms and logical operators from the windows. The server may further include a search engine configured to perform at least one of a direct search or a contextual search for an entered query string in records stored in the database and the client may include a visual interface for displaying results of the searches. The search results generated by the search engine may be stored as terms in the database for subsequent rule generation.

An exemplary embodiment of the present invention includes a method for searching electronic records and displaying relevant data based on the search. The method includes entering a query string, searching for unique occurrences of text in the electronic records that are within a context of the query string, wherein a context comprises text that precedes or follows the entered query string in the electronic record that influences the meaning of the query string, and displaying each of the unique occurrences of text. The method may further include maintaining a count of each of the unique occurrences and displaying each corresponding count along with the unique occurrences.

BRIEF DESCRIPTION OF THE DRAWINGS

Exemplary embodiments of the invention can be understood in more detail from the following descriptions taken in conjunction with the accompanying drawings in which.

DETAILED DESCRIPTION OF EXEMPLARY EMBODIMENTS

In general, exemplary systems and methods for contextual searching of electronic records and visual construction of rules will now be discussed in further detail with reference to FIGS. 1-10. It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying figures are preferably implemented in software, the connections between system modules (or the logic flow of method steps) may differ depending upon the manner in which the present invention is programmed. Given the teachings herein, one of ordinary skill in the related art will be able to contemplate these and similar implementations of the present invention.

Figure 1A:
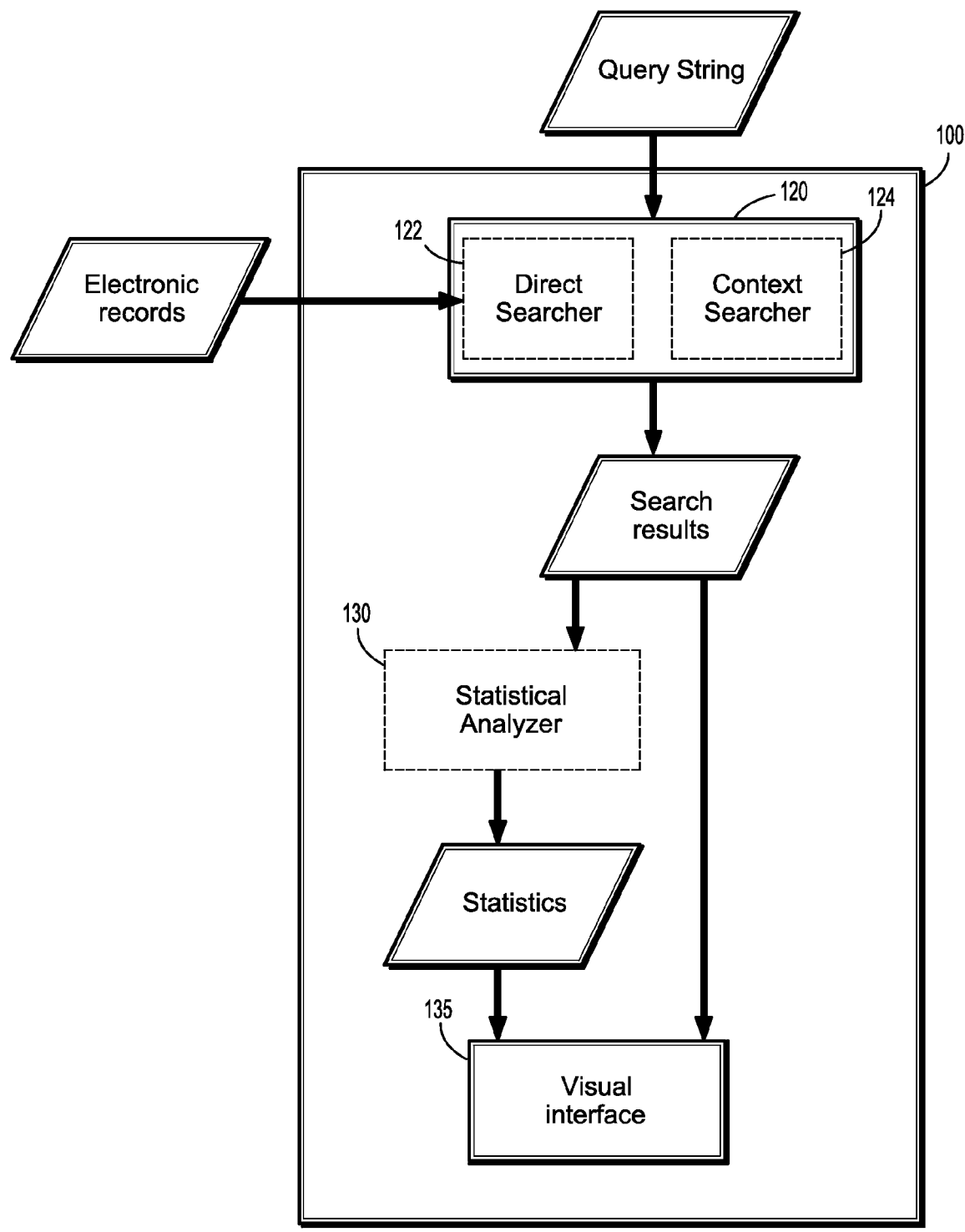
FIG. 1A illustrates a high-level block diagram of a system that searches electronic records and displays data relevant to the search according to an exemplary embodiment of the present invention.

FIG. 1A illustrates a high-level block diagram of a system that searches and retrieves data from electronic records according to an exemplary embodiment of the present invention. The electronic records may include medical records, financial records, legal records, etc. Referring to FIG. 1A, the system is a searching unit 100, which includes a search engine 120 and a visual interface 135. The searching unit 100 includes a context searcher 124 and may optionally include a direct searcher 122. The searching unit 100 may optionally include a statistical analyzer 130. The searching unit 100 can perform off-line indexing of all text reports from multiple patient databases. In this way, when a user later queries a large database, the off-line index can be used to quickly provide the results.

The context searcher 124 searches electronic records based on an entered query string to return search results that are within a context of the entered quest string. The entered query string can be a regular expression. The search results corresponding to the context may include parts of a written statement (e.g., sentence) that precede or follow a specific word or words (e.g., the entered query string), which may influence its meaning or effect. The context searcher 124 can perform an aggregate search by searching for contexts of one or more types. For example, the context types may include a phrasal context (e.g., non-list, sentences, or parts of sentences), bullet context (e.g., bullets in text), and list context (e.g., sentence/paragraph that contain inline lists).

The direct searcher 122 searches the electronic records directly for the entered query string to return search results that include the entered data. For example, the search results may include the documents that include the entered query string. For example, the search results may include the documents that have the most frequent occurrence of the entered query string. The direct searcher 122 may also return search results at a lower granularity such as parts of documents (e.g. a paragraph, sentence) that include the entered query string.

The statistical analyzer 130 can analyze the search results to calculate various statistics. For example, the statistical analyzer 130 can calculate occurrences of an entered query string in an electronic record and occurrences of contexts associated with the entered query string in an electronic record. The statistical analyzer 130 may also calculate statistics relating to the type of electronic record or the institution the electronic record came from. For example, 90% of electronic records of a first type may include contexts associated with entered query string, while only 30% of the electronic records of a second type may include those same contexts. In a further example, 70% of electronic records from a first institution may include documents including the entered query string, while only 10% of the electronic records from a second institution may include similar such documents. The visual interface 135 presents the search results to a user. When the statistical analyzer 130 is included, the visual interface 135 also presents any corresponding statistics.

Logical rules (e.g., best fit rules) can be derived from the search results to perform more re-fined data mining. The logical rules can be used by various systems, such as a reasoning system, a classifier system, an extraction system, etc. The logical rules may be written in a format used by native computer systems. For example, Unix includes a grep search command, and web-based systems can perform searches using XML. However, a typical user may not be skilled in the necessary formats.

Figure 1B:
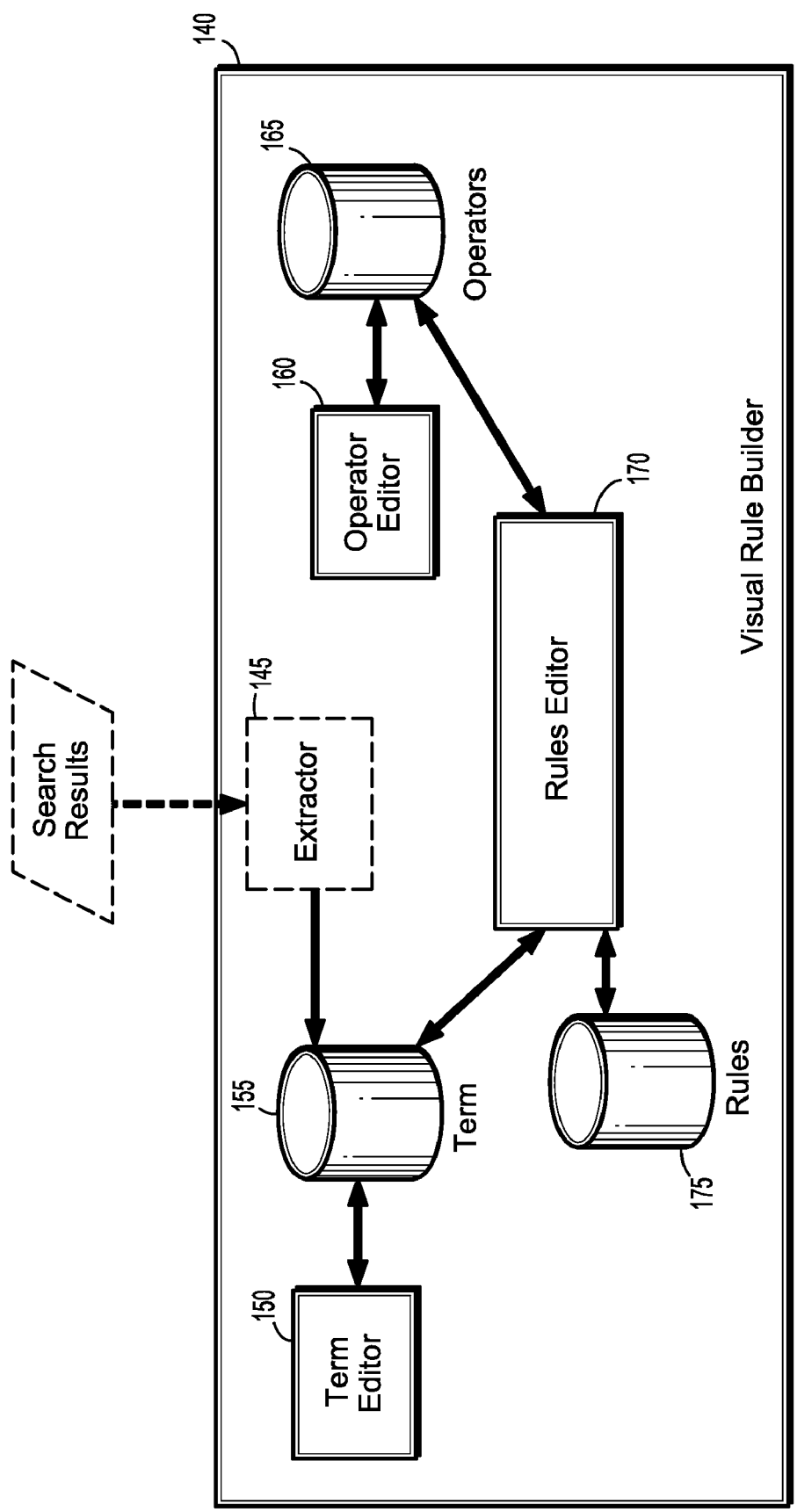
FIG. 1B illustrates a high-level block diagram of a system that enables a user to visually construct logical rules according to an exemplary embodiment of the present invention.

FIG. 1B illustrates a high-level block diagram of a system that enables a user to visually construct logical rules according to an exemplary embodiment of the present invention. The system is a visual rule builder 140 and a user need not be skilled in any particular format to use the rule builder to generate rules. The visual rule builder 140 may optionally work in concert with the system of FIG. 1A or in a stand-alone fashion. For example, the search results provided by the searching unit 100 can be used by the visual rule builder 140 in the construction of rules.

The visual rule builder 140 includes provides for storage of terms and connecting operators, which may be used to visually construct one or more rules. The visual rule builder 140 further provides storage for the constructed rules. FIG. 1B illustrates the visual rule builder 140 including a term database 155 for storing terms, an operator database 165 for storing the operators, and a rules database 175 for storing the database. However, the terms, operators, and rules may be stored in various ways (e.g., in a single database, in memory, as flat files, etc.). FIG. 1B illustrates the visual rule builder 140 including a term editor 150 for editing terms, an operator editor for editing the operators, and a rules editor 170 for editing the rules. However, the terms, operators, and rules may be edited using a single editor. The editors 150, 160, 170 are visual editors, which comprise one or more graphical windows. For example, the term editor 150 may include a selectable window of terms, the operator editor 160 may include a selectable window of operators, and the rules editor 170 may include a selectable window of rules constructed from the terms and operators. The visual construction of rules using the visual rules builder 140 will be described later in more detail with respect to FIGS. 3-9.

Figure 1C:
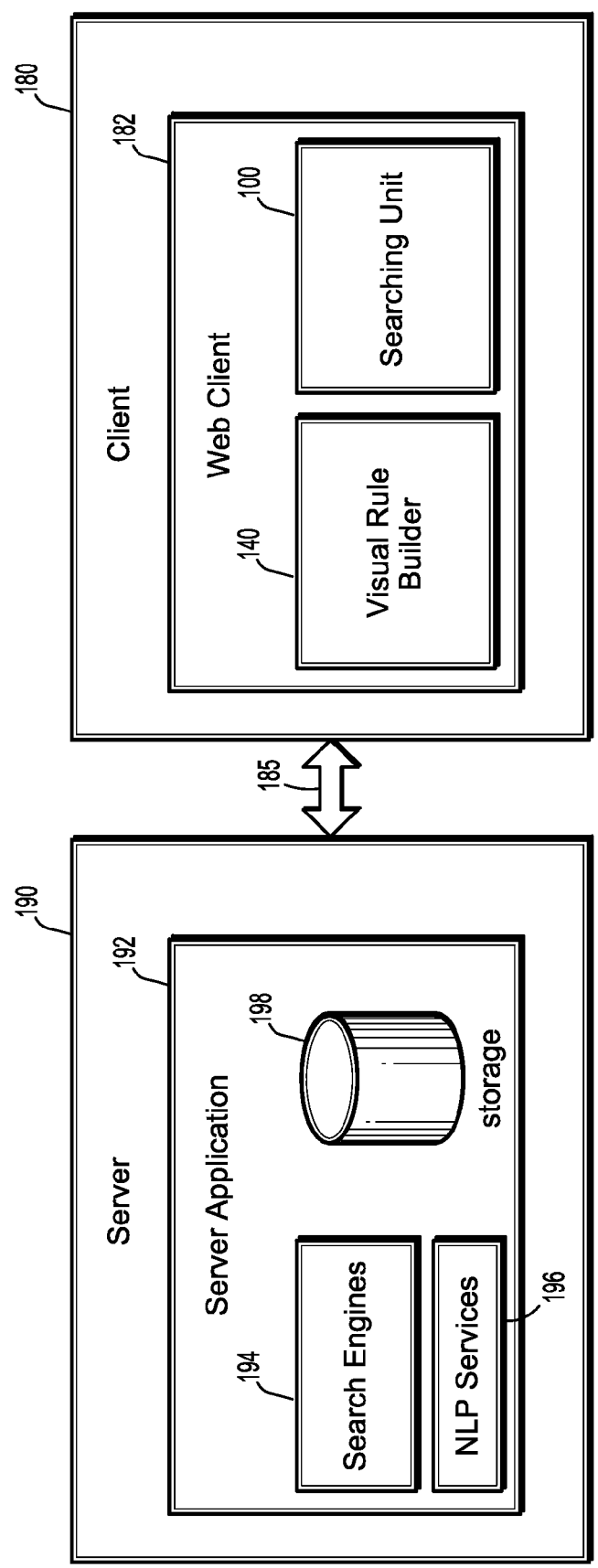
FIG. 1C illustrates a high-level block diagram of a web-based system according to an exemplary embodiment of the present invention that includes the systems of FIG. 1A and FIG. 1B.

FIG. 1C illustrates a high-level block diagram of a web-based system according to an exemplary embodiment of the present invention that includes the systems of FIG. 1A and FIG. 1B. Components or portions of each of the systems of FIGS. 1A and 1B may be embodied a stand-alone web-applications, such as an RIA (Rich Internet/Web Application) application on a server 190 and a remote client 180 distributed over a network 185. Multiple clients can run their corresponding client-based web-applications. For example, the client 180 can use run the web-applications using a local browser. Since the client 180 is web-based it can be platform independent. Other more computationally intensive portions of the systems (e.g., searching) can be offloaded to the server 190. The server 190 may be modular and may use an XML-RPC (remote procedural call) for asynchronous communication. The client-sever approach allows down-time to be minimized or eliminated. For example, the client 180 may continue to run with an older version of the server-based components until the current server-based components have been upgraded.

While FIG. 1C illustrates the web client 182 may run both the visual rule builder 140 and the searching unit 100, each of the web-applications are stand-alone applications, and the web client 182 may run them individually. When the systems of FIGS. 1A and 1C are embodied as web-applications, storage of the terms, rules, operators, and electronic records may be provided by storage 198 on the server 190. Further, functions illustrated as being provided by the systems of FIGS. 1A and 1B may be provided by a server application 192 on the server 190. For example, the searching unit 100 may use search engines 194 on the server 190 to perform its direct searching and context searching.

Each of the systems of FIGS. 1A and 1B may also provide services for handling morphological variants. For example the searching unit 100 may be configured to perform searches on morphological variants of an entered query string or the visual rule builder 140 may be configured to construct rules using morphological variants of the terms. The services for handling morphological variants may be off-loaded to the server application 192. For example, natural language processing (NLP) services 196 of the server application 192 may be used to handle the morphological variants.

Examples of morphological variants include part of an entered query string, term, or a related string or term, such as a synonym, hypemym, hyponym, inflection, etc. A hyponym is a word or phrase whose semantic range is included within that of another word. For example, scarlet, vermilion, carmine, and crimson are all hyponyms of red, which is, in turn, a hyponym of colour. The term hypemym denotes a word, usually somewhat vague and broad in meaning, which other more specific words fall under or are fairly encompassed by. For example, vehicle denotes all the things that are separately denoted by the words train, chariot, dogsled, airplane, and automobile and is therefore a hypemym of each of those words. Inflections are endings that change the form of a word for a grammatical category without changing its grammatical class. Thus sadder and saddest contain inflections for the grammatical categories of comparative and superlative but the words remain adjectives, whereas the word sadness contains a derivational form that changes the word to the class noun.

Figure 2A:
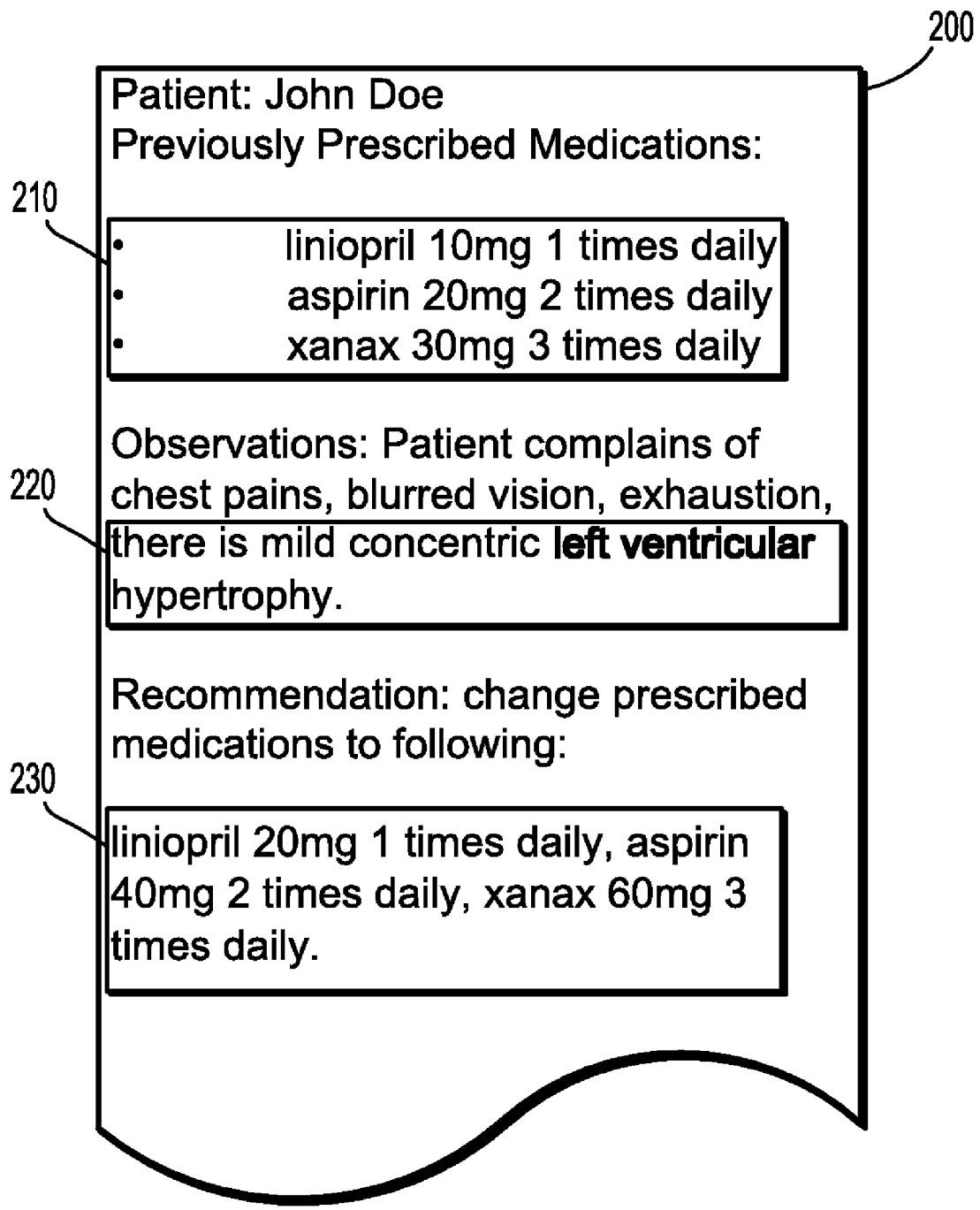
FIG. 2A illustrates an example of a medical record that may be searched by the system of FIG. 1A.
Figure 2B:
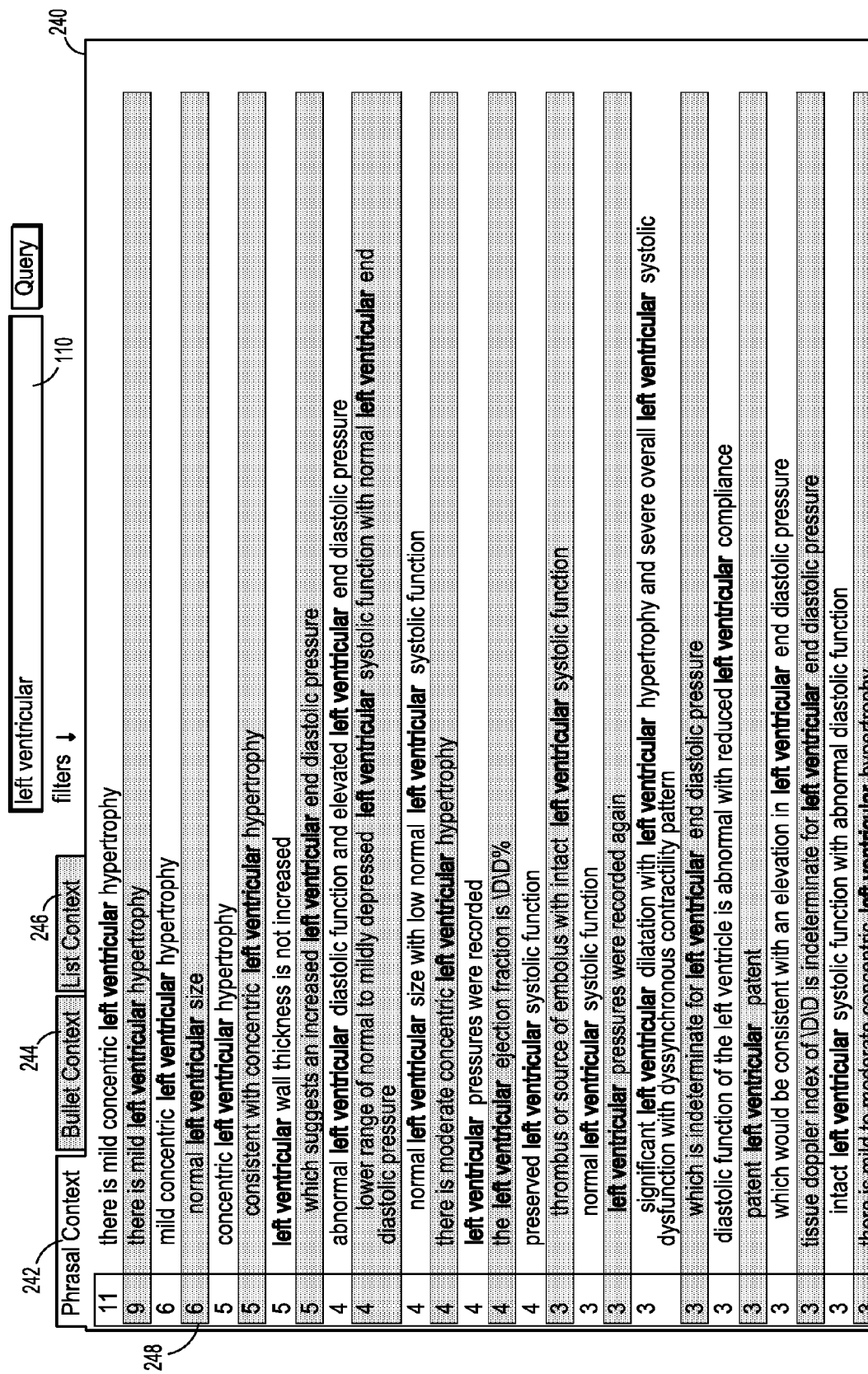
FIG. 2B illustrates an exemplary embodiment of a visual interface of the system of FIG. 1A.

FIG. 2A illustrates an example of a medical record 200 and FIG. 2B illustrates an exemplary context window 240 of the visual interface 135 of FIG. 1A, which may be used by the searching unit 120 to present context results. As shown in FIG. 2B, the context results may include phrasal contexts 242, bullets contexts 244, and list contexts 246. The context searcher 124 can search (e.g., parse) medical records for phrases that are within the context of the entered query string while the statistical analyzer 130 can extract statistics based on the returned phrases.

For example, strings that precede and follow the entered query string may be considered phrasal contexts 242. The context searcher 124 may use ordinary punctuation (e.g., a period, colon, semicolon, comma, spaces, etc.) in a medical record to differentiate between the phrasal contexts 242 associated with an entered query string and the rest of the medical record. The context searcher 124 can locate each instance of the entered query string in the medical record 200, extract the text preceding each instance up to a preceding point of punctuation, the instance itself, and the text following the instance up to a next point of punctuation to arrive at the resulting phrasal contexts 242. The statistics may include the frequency of occurrence of the phrasal contexts 242 within a single medical record, within multiple records, or within medical records of a particular type.

The following example will be used to describe phrasal contexts 242. In this example, it will be assumed that the string "left ventricular" is the entered query string. As shown in FIG. 2A, the exemplary medical record 200 includes the phrase "left ventricular" and the phrase "there is mild concentric left ventricular hypertrophy" 220. The phrase 220 may have been determined to be a phrasal context 242 using the delimiting punctuation (e.g., the preceding comma and the following period). FIG. 2B illustrates further examples of phrasal contexts 242 that may be returned by the context searcher 124 when other medical records are searched for the same entered query string.

FIG. 2B illustrates tabs in the context window 240, that may be used for displaying bulleted contexts 244 and list contexts 246. The next example will be used to illustrate bullet contexts 244 and list contexts 246. In this example, it will be assumed that the entered query string is "aspirin". The list of prescribed medications for a patient may be found in a bulleted list or in a simple list (e.g., where elements are separated by commas) in a medical record. In this way, entering a query string for a single medication can return an entire list of prescribed medications, thereby enabling a user to review prescribed medications, evaluate drug interactions, etc. FIG. 2A illustrates an exemplary string 210, which may appear as a bulleted context 244 in the context window 240 when the entered query string is "aspirin". FIG. 2A further illustrates an exemplary string 230, which may appear as a list context 246 in the context window 240 when the entered query string is "aspirin". The context searcher 124 may search for other list-like contexts. For example, lists may include indented terms, terms with preceding dashes, numbered terms, etc.

The search results from multiple patients can be combined based on co-occurrence statistics. For example, the context window 240 may display statistics 248, such as the frequency of occurrence of the phrasal contexts 242. The phrasal contexts 242 may be ordered based on these statistics (e.g., based on frequency of occurrence) in the searched medical records. For example, FIG. 2B illustrates that searching for "left ventricular" in the medical records returned 11 instances of "there is mild concentric left ventricular hypertrophy". Although not shown in FIG. 2B, the context window 240 may also display similar statistics for the bulleted and list contexts 244 and 246.

The context searcher 124 may be configured to hide personal information from display. For example, if a phrasal context includes a patient name, this information can be suppressed. The context searcher 124 may narrow its search based on entered or pre-defined constraints. For example, the search can be constrained based on medical record type, a named medical institution, etc. Further, the presentation of the context results and associated statistics 248 in the context window 240 can be filtered at different levels such as: patient level, visit level, document level, paragraph level, and snippet level. The data filtering can also be performed at a physician/nurse level, patient group level, as well as to a specific institution or computing system. Inter-institution comparisons and statistics can be acquired when multiple institutions are involved. This search enables a user to retrieve pertinent common contexts in patient records.

Structural matching can be performed using exact or inexact matching methods (e.g., where the level of exactness can be specified). For example, the context searcher 124 can be set up to search for part of an entered query string, or a related string, such as synonym, hypemym, hyponym, inflection, etc.

The search results of FIG. 1A may be sent to the visual rule builder 140. The search results can be stored as terms in the terms database 155 for subsequent generation of logical rules. Since the search results may include multiple strings, they may be further subdivided into constituent terms for storage as terms in the terms database 155. For example, when the search results include more than a single string or term, an extractor 145 can be used to extract pertinent individual elements from a string of the search results. For example, the pertinent elements of the phrasal context, "there is mild concentric left ventricular hypertrophy", may be considered "mild", "concentric", "left", "ventricular", and "hypertrophy". The extractor 145 may skip connecting terms such as "there" and "is". The extracted elements can then be added as terms to the terms database 155, if they are not already present.

However, the extractor is optional 145, as the visual rule builder 140 is a stand-alone application, and does not require external input from the searching unit 100. The rules editor 170 of the visual rule builder 140 can be operated by a user to select desired terms from the terms database 155 and operators from the operator database 165 to construct various rules. While terms have been described as including one or more strings, terms may additionally include an entire sentence, paragraph, document, body of documents. The term database 155 may include pre-loaded terms. The rules editor 170 may be used to select terms from the pre-loaded terms or terms manually entered through the terms editor 150. The operator database 165 may include pre-loaded operators and additional operators may be added using the operator editor 160. The constructed rules can then be stored in the database of rules 175. Once the rules have been created, a subsequent user can load a pre-defined rule and modify it for the user's intended purpose. The modified rule can then be stored with the changes or saved as a new rule. Rules may be shared by multiple users.

A user can use a rule from the rules database 175 to perform a search on electronic records (e.g., medical, financial, legal, etc.). While records, rules, operators, and terms have been described above as being stored in databases, each may be stored in flat files, memory, arrays, stacks, structures, linked lists, etc.

The visual rule builder 140 enables a user to visually transform textual information into complex desired logical rules. The visual rule builder 140 enables the construction of complex logical patterns that may be difficult to write in terms of formatting and correctness. Since the rules are constructed in a visual fashion, the user needs no knowledge of the underlying language that the rules are constructed within. For example, the underlying language could be XML. The visual rule builder 140 may include a visual interface (e.g., web-based) for enabling a user to create and manipulate an entire logical structure via intuitive drag-n-drop, context menus, and parameter editing functions. The data extracted by the visual rule builder 140 can be used to draw inferences (e.g., make a diagnosis, check for drug interactions, medical billing, determine candidates for drug trials, etc.). The generated rules (e.g., XML rules) can enable domain knowledge engineers to quickly and intuitively create and modify rules for phrase spotting and document splitting, as well as other types of knowledge enabled components that require expert rules as part of a model building process.

The visual interface is paradigm for constructing, manipulating and compiling complex knowledge-driven systems that include rule-based classification components, rule-based extraction components, expert components, as well as logical and reasoning components. The visual interface enables an intuitive and visual user driven hierarchical construction of such systems. The paradigm allows for rich elements and parameterized operators to easily be embedded into rules and logical structures. The interface is not dependent on a particular knowledge-specific language and can accommodate knowledge-enhanced programming language constructs.

The interface presents an interactive graphical user interface, supporting the definition, manipulation, maintenance, and reuse of structured text and logic-based artifacts, such as pattern matching rules or programming languages. The structure is mapped to a hierarchical tree, where one node corresponds to standalone elements of the language. Advanced interactive operations are supported on the tree, allowing the user to efficiently perform operations which would be complex, error-prone and effort intensive if performed on a textual or traditional programmatic representation.

The interface permits a user to construct and parameterize the logic and the operator interaction into rules, and then through an adaptor, compile such a rule system into a specific programming or data language (e.g. XML). In the case of XML, the interface may use the known hierarchical structure of XML to represent the rules in the form of an interactively editable tree. A similar representation could be used for representing other hierarchically structured representations, such as Java, C, or C++ programs.

Figure 3:
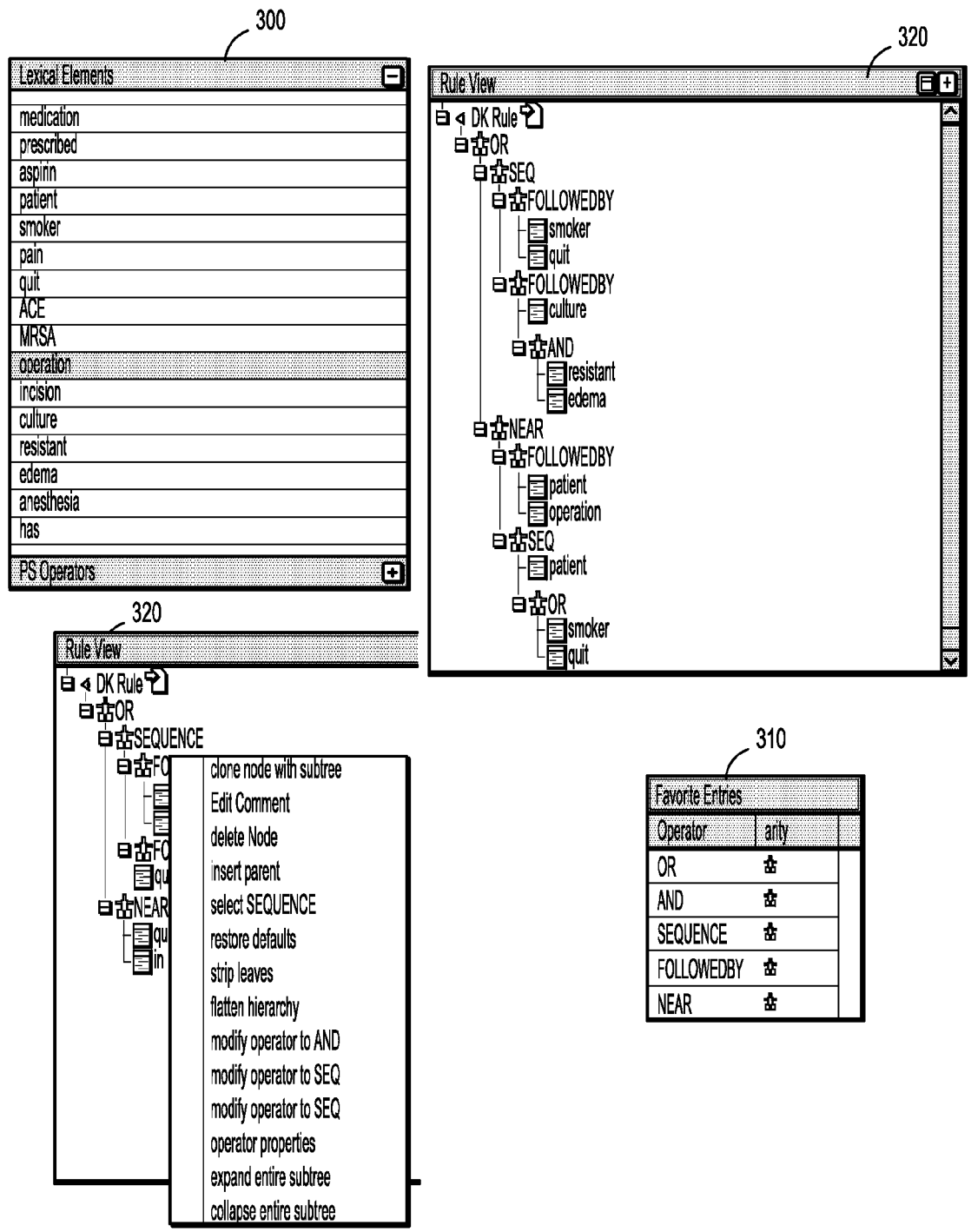
FIG. 3 illustrates visual interfaces of the system of FIG. 1B according to an exemplary embodiment of the present invention.

FIGS. 3-9 illustrates an embodiment of the visual interface according to an exemplary embodiment of the present invention. Referring to FIG. 3, the interface includes a lexical element window 300, an operator element window 310, and a rule view window 320. The visual interface may further include an operator-specific context menu 330. The lexical element window 300 lists one or more lexical elements available in the term database 155. The lexical element window 300 enables access to the term editor 150, so that new terms can be manually entered. An existing term or lexical element can be modified or deleted and a new term or lexical element can be added using the term editor 150.

Figure 4:
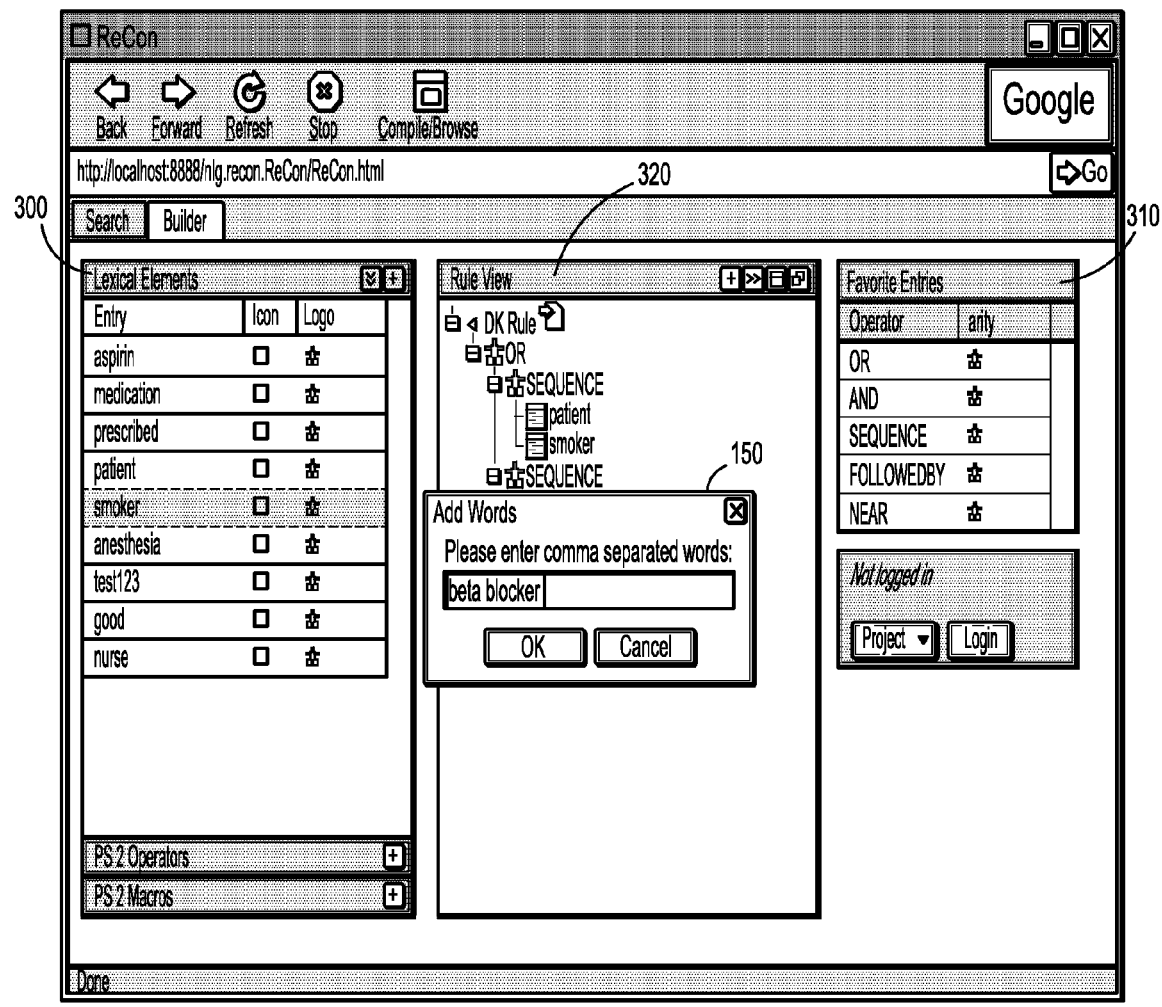
FIG. 4 illustrates an exemplary embodiment of a term editor of FIG. 1B.

FIG. 4 illustrates an exemplary embodiment of the term editor 150 being used to add a new term (e.g., "beta blocker") to the term database 155. The term editor 150 can be opened in various ways. For example, an option menu (e.g., with choices of add, delete, modify, etc.), may be provided when right-clicking over an area of the lexicon element window 300 to display the term editor 150. The term editor 150 may include a text field for entering/modifying the corresponding lexical element or term.

The operator element window 310 lists one or more operators available in the 2) operator database 165. The operator element window 310 enables access to the operator editor 160. The operator editor 160 operates in a similar manner to the term editor 150, allowing new operators to be manually deleted, modified, or added. The operators may include terms that connect one or more terms or lexical elements into a rule that can be executed to search for data in the records. The operators may specify a hierarchical ordering of the terms or lexical elements within a record. For example, the operator set may include the following operators: "OR" (specifying that one or the other term should appear), "AND" (specifying that both terms should appear), "SEQUENCE" (specifying that the terms should be in a sequence), "FOLLOWEDBY" (specifying that one term should follow another), "NEAR" (specifying that one term should be near another), etc.

The rule view window 320 lists one or more rules available in the rules database 175. For example, a part of the rule illustrated in FIG. 3 specifies a rule for determining whether "smoker" is followed by "quit" and whether "culture" is followed by "resistant" and "edema" in a medical record. The rule view window 320 offers a tree-based view of the rules, where operators are nodes of the tree and terms or lexical elements are leaves of the tree.

The visual interface may also provide an XML-based view (not shown) of a rule. For example, as discussed above, the rules may be written in an underlying language such as XML. The XML-based view provides a view of the rule in XML and allows the rule to be edited manually using XML specific keywords. The XML-based view can show the updated rule in XML as a result of user manipulations in the tree-based view. The rule can be manipulated/extended in any view and kept synchronized with the other view.

As shown in FIG. 3, the operator-specific context menu 330 may be used to clone an operator and its children (e.g., with all parameterization/customization information), edit or add a comment to an operator, term, or lexical element, delete an operator, insert an operator as a parent, select an a sequence of operators, restore parameters of an operator or child lexicon to a default state, delete (e.g., strip) all of the leaves of an operator, remove an operator and move its children to a higher level within the rule hierarchy (e.g., flatten hierarchy), modify an operator, edit operator or lexicon parameters, alter presentation of an operator (e.g., expand sub-tree to show children or collapse sub-tree to hide children), setup lexicon variations, etc. The menu may also include a function to allow a new node to be dragged into the tree, where the target parent node automatically expands to show the new child node in context of where it was inserted. The menu 330 may not include all of the above described functions. Further, the menu 330 may include additional functions.

Figure 5:
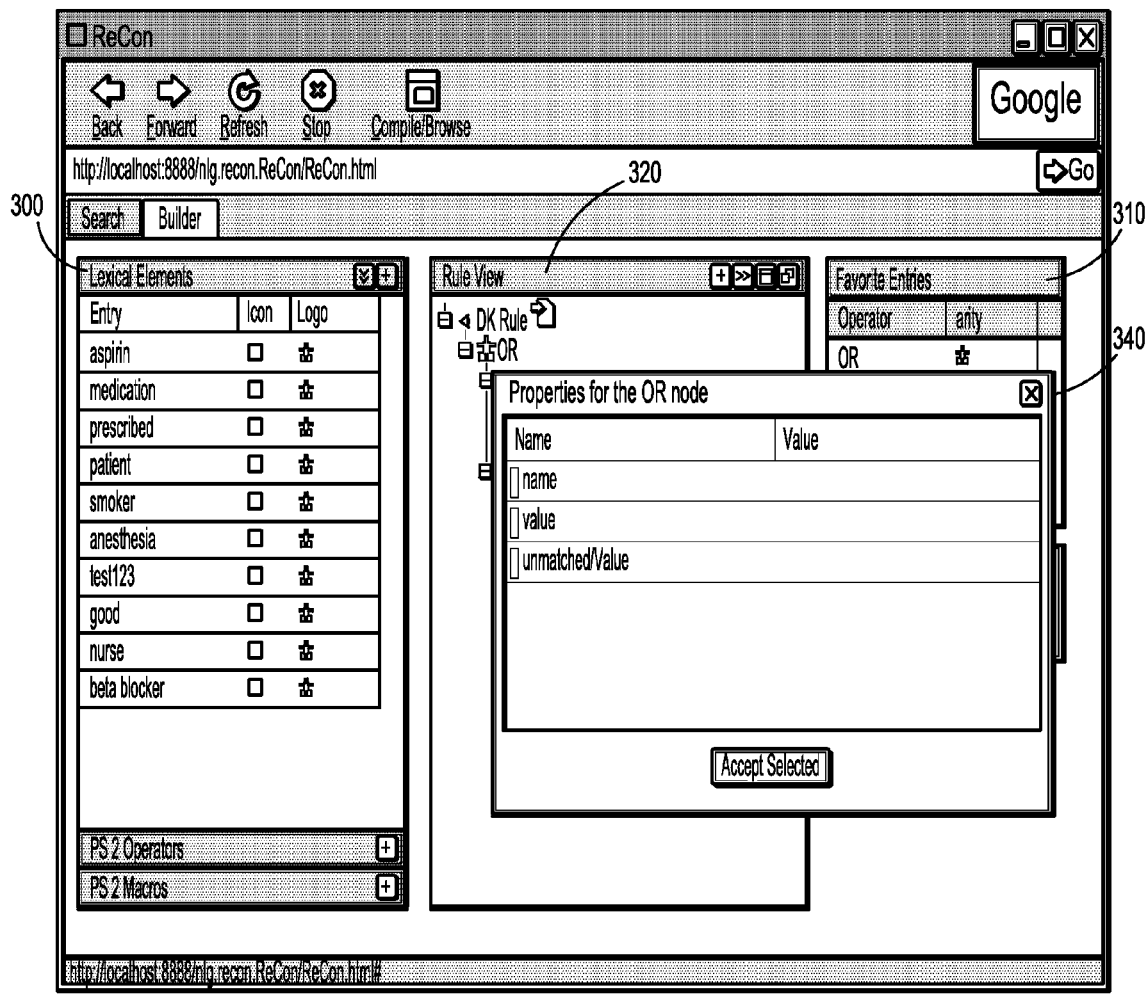
FIG. 5 illustrates an exemplary embodiment of an operator properties window of a visual interface of FIG. 3.
Figure 6:
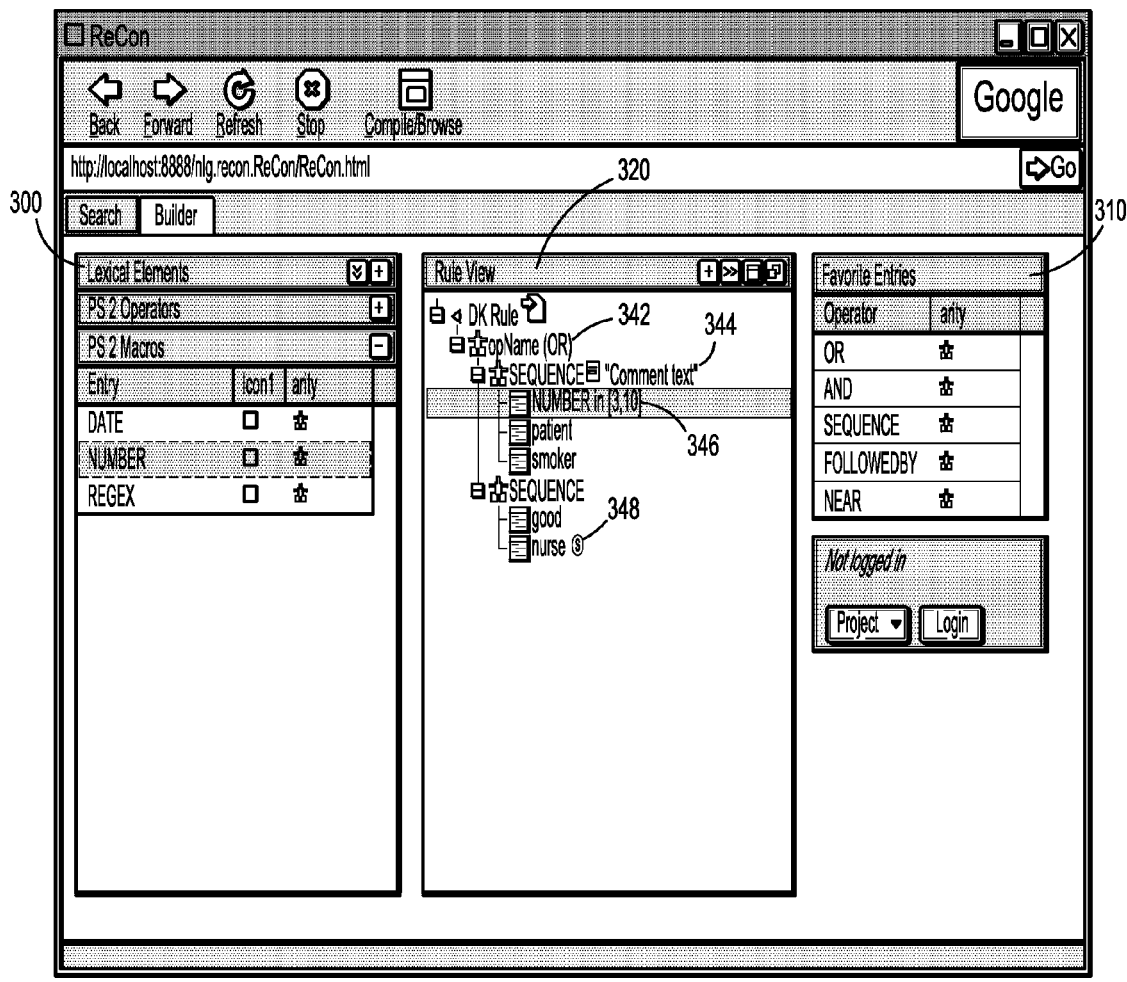
FIG. 6 illustrates exemplary parameters, comments, and an error indicator that may be displayed in a rule view window of the visual interface of FIG. 3.

FIG. 5 illustrates an exemplary embodiment of an operator properties window 340, which may be used to edit operator parameters (e.g. name, value, etc.). FIG. 6 illustrates an example of a name parameter 342 (e.g., "opName), which may be added to an operator, and a value parameter 346 (e.g., "[3,10]"), which may be added to a lexicon "NUMBER". In this example, the rule specifies a number ranging from 3 to 1.0 in a medical record.

FIG. 6 further illustrates a comment 342, which may be added to an operator. The visual rule builder 140 may perform structural and parameter validation on the rule nodes and expressions (e.g., sub-trees), and denote any error by decorating the tree node icons for the error nodes, and their parents. For example, FIG. 6 further illustrates an exemplary icon 348, which may be used to indicate that the node, sub-tree, or rule has an error.

Figure 7:
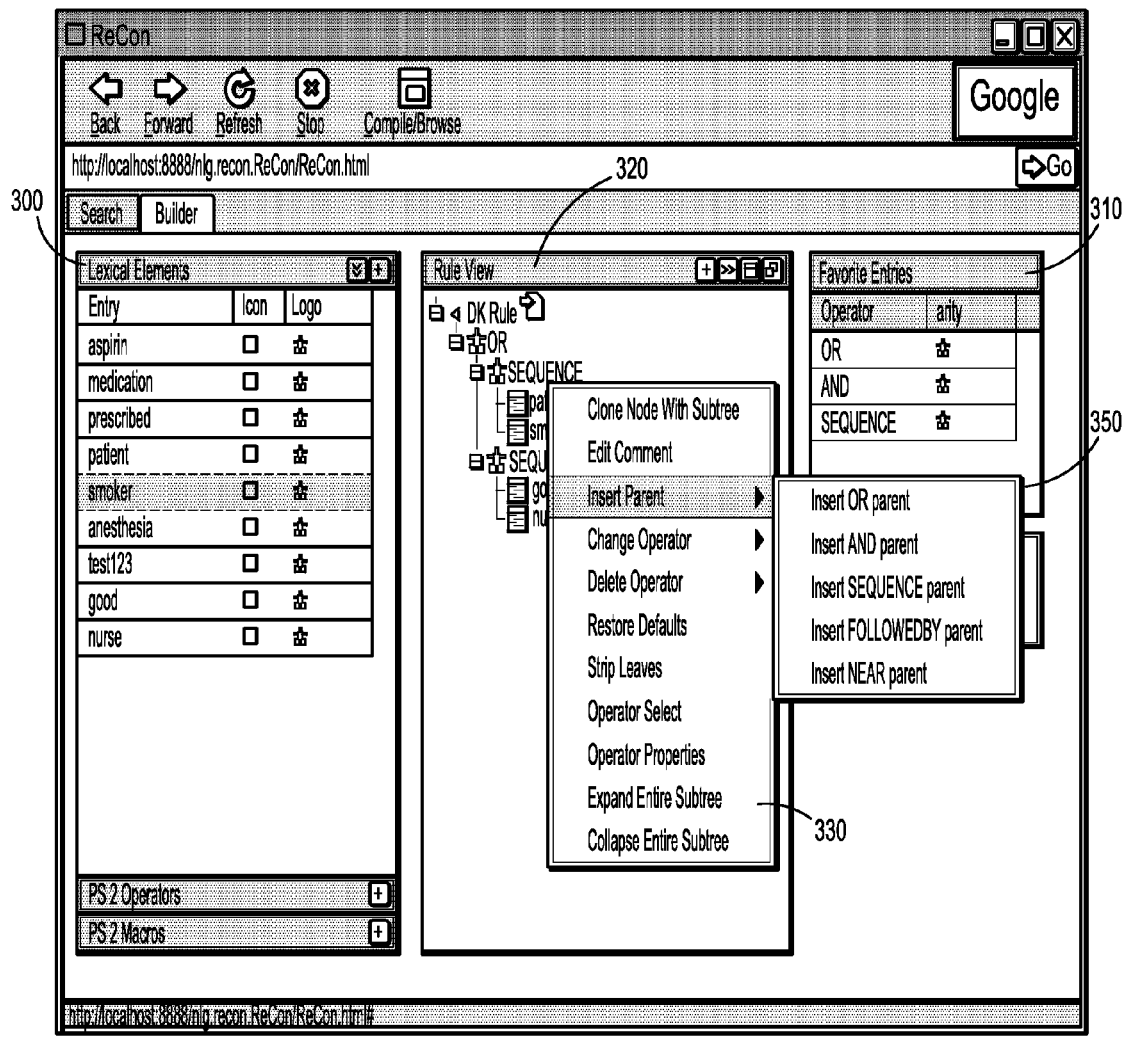
FIGS. 7-9 illustrate exemplary embodiments of an operator context menu of the visual interface of FIG. 3.

FIG. 7 illustrates an embodiment of an insert parent menu 350, which may be launched by the operator-specific context menu 330. The insert parent menu 350 may be used to add a new operator as a parent node to a selected node (e.g., existing node becomes a child of new node) in a selected rule in the rule view window 320. The insert parent menu 350 may include choices for inserting one or more operators (e.g., OR, AND, SEQUENCE, FOLLOWEDBY, NEAR, etc.) from the operator database 165 as new parent nodes. The insert parent menu may also be used to add a joint parent to several existing sibling nodes in the tree (e.g., new node becomes child of the former parent node of the sibling nodes, and the sibling nodes become the children of the new node)

Figure 8:
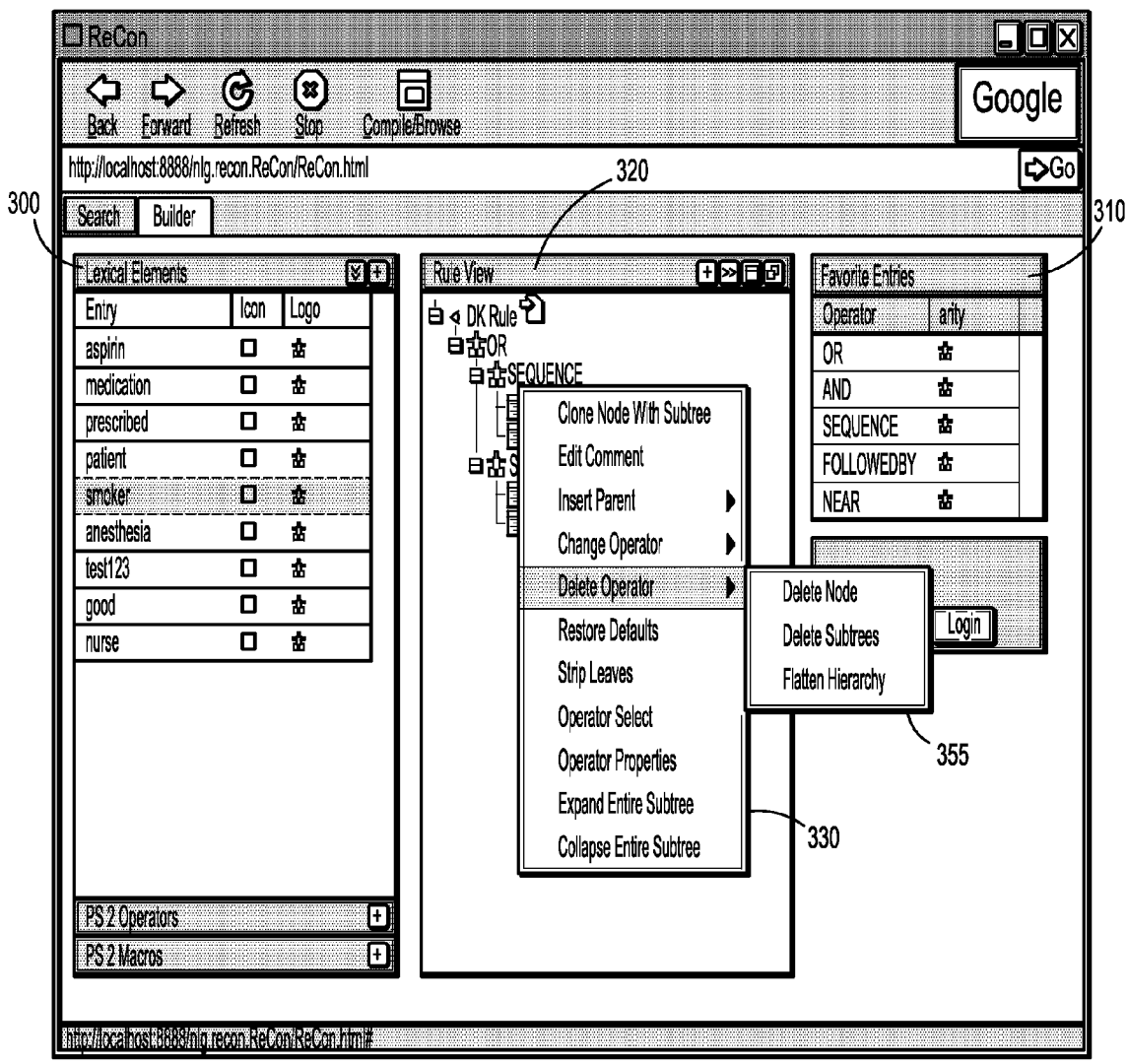

FIG. 8 illustrates an embodiment of a delete operator menu 355, which may be launched by the operator-specific context menu 330. The delete menu 355 may be used to delete a node, lexicon, or a sub-tree in a selected rule in the rule view window 320. The delete menu 355 may be used to remove all children of a selected tree node with a single selection (e.g., without removing the selected node). The delete menu 355 may also be used to remove a parent node, while keeping its children in the system tree hierarchy (e.g., nodes move up to their previous grand-parent node). The delete menu 355 may also be used to remove all leaf customization nodes from a sub-tree, leaving a pattern for reuse.

Figure 9:
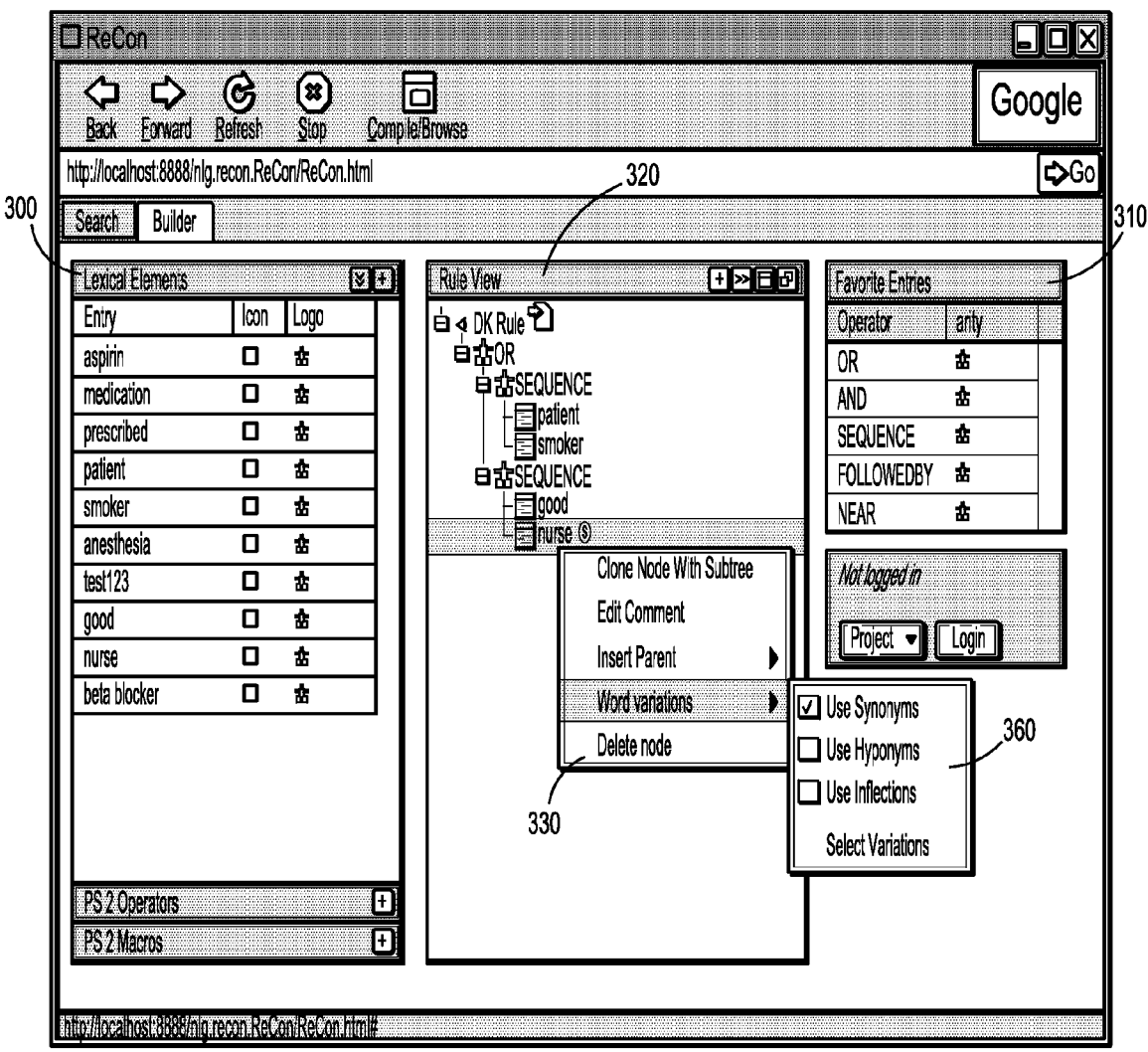

FIG. 9 illustrates an embodiment of a variations menu 360, which may be launched by the operator-specific context menu 330. The variations menu 360 enables a rule to specify word variations for constituent terms or lexical elements. For example, each term or lexical element added to a rule can specify one or more possible word variations, such as parts of the term or lexical element (e.g., using wild cards), synonyms, hypernyms, hyponyms, inflections, etc.

The visual interface may allow restoring of all nodes in a subtree to a default state, and the removing of parameterization information. The visual interface may indicate tree structure definition and node customization errors in the tree nodes, and inheritance by their parent nodes. The visual interface may enable commenting/un-commenting an existing hierarchical node without removing it from the structure. The visual interface may enable node operators to be modified/replaced without impacting the sub-trees.

The visual interface may support filtering of available terms, lexical elements, rules, or operators. For example, a function to specify favorite terms, lexical elements, rules, and/or operators may be provided. Further, the visual interface may provide a function for selecting which nodes of a rule to hide or show. The menus provided by the visual interface may be node-specific. For example, a node-specific context menu associated with multiple selected nodes in a tree, based on their type and structural relationship may be provided (e.g., different menu if nodes are siblings or not).

The visual interface may provide a capability to customize terms or lexical elements, before dragging their instances into a tree-based rule. Terms or lexical elements may be replicated and customized differently for each rule. The visual interface may provide a capability to use customized nodes in a tree-based rule, and to paste them as templates. The visual interface may provide a capability to perform operator distribution transformations, within semantic rules for the system (e.g., functions for converting Seq(Or, Or) into OR(Seq, Seq, Seq, Seq) or vice versa).

The visual rule builder 140 may support modification of individualized rules that can apply to specific institutions with specific clinical writing/dictation guidelines, styles, policies, which may differ from other institutions. The rule builder 140 may be integrated with a server-side processing analysis engine that may include providing semantic lists (e.g. for semantic expansion), a hierarchical or non-hierarchical category structure/ontology (e.g. cephalothin is a medication). The system logical manipulation structure supports the embedding of domain specific entities and types of text patterns/classes (e.g., numbers, units, etc.), both in terms of manipulation and displaying. The rule builder 140 can integrate with server-supplied domain specific entities and types of text patterns/classes (numbers, units etc). These entities may be computed and provided to the rule builder 140 based on back-end server processing. The rule builder 140 may support user defined phrases/expressions and word sets, and regular expressions(e.g., PS2 regular expression syntax). The rule builder 140 may support access to persistent storage facilities (e.g., individual and shared). The rule builder 140 may be integrated with shared persistent storage. The rule builder 140 may be initialized with context specific entries, creating rule skeletal structures (e.g., empty vs. learned vs. full pre-fill, user options, etc). The rule builder 140 may support multiple simultaneous users. During the rule building process, the rule builder 140 can learn user patterns and pre-fetch certain rule structures or propose likely initial rule skeletal structures. The learning can be done based on one user or a collaboration of multiple users.

During rule development, a user may explore various statistics of the context (e.g., phrase) for which the rule is being built. The searching unit 100 may be part of a back-end server, which may provide information such as the frequency of the phrase being addressed, the distribution of the origin of the phrase, as well as information about other public rules previously built by the same user or other users for the same or similar phrase.

The frequency information encodes the relevance of the rules being built. For example if the phrase occurs very frequently in the records, the rule covering this phrase is more likely to be relevant and thus more likely to be useful. However, if the phrase is rare used in the records, the rule may not apply to most cases, and thus may be utilized less.

Another set of statistics relates to distributions over the origin of a particular contextual phrase. For example, the user may benefit from knowing the frequency over the type of documents for the particular phrase (e.g. 50% discharge summaries, 21% pathology reports, 29% other, etc.). The availability of distribution information over specific institutions can enable a user to optimize coding the rules for typical phrases that span multiple institutions.

Exemplary embodiments of the searching unit 100 and the visual rules builder 140 can be applied to frequently used context types and can be extended to new contextual paradigms. The searching unit 100 and the visual rules builder 140 may be scalable to large patient record databases. Embodiments of the searching unit 100 and the visual rules builder 140 may be used to perform efficient dataset exploration for expert rule construction (e.g. building domain knowledge), comparative studies for specific datasets (e.g., patient record databases), clinical trial filtering, dynamic rule generation based on statistically pooled context evidence, etc.

Figure 10:
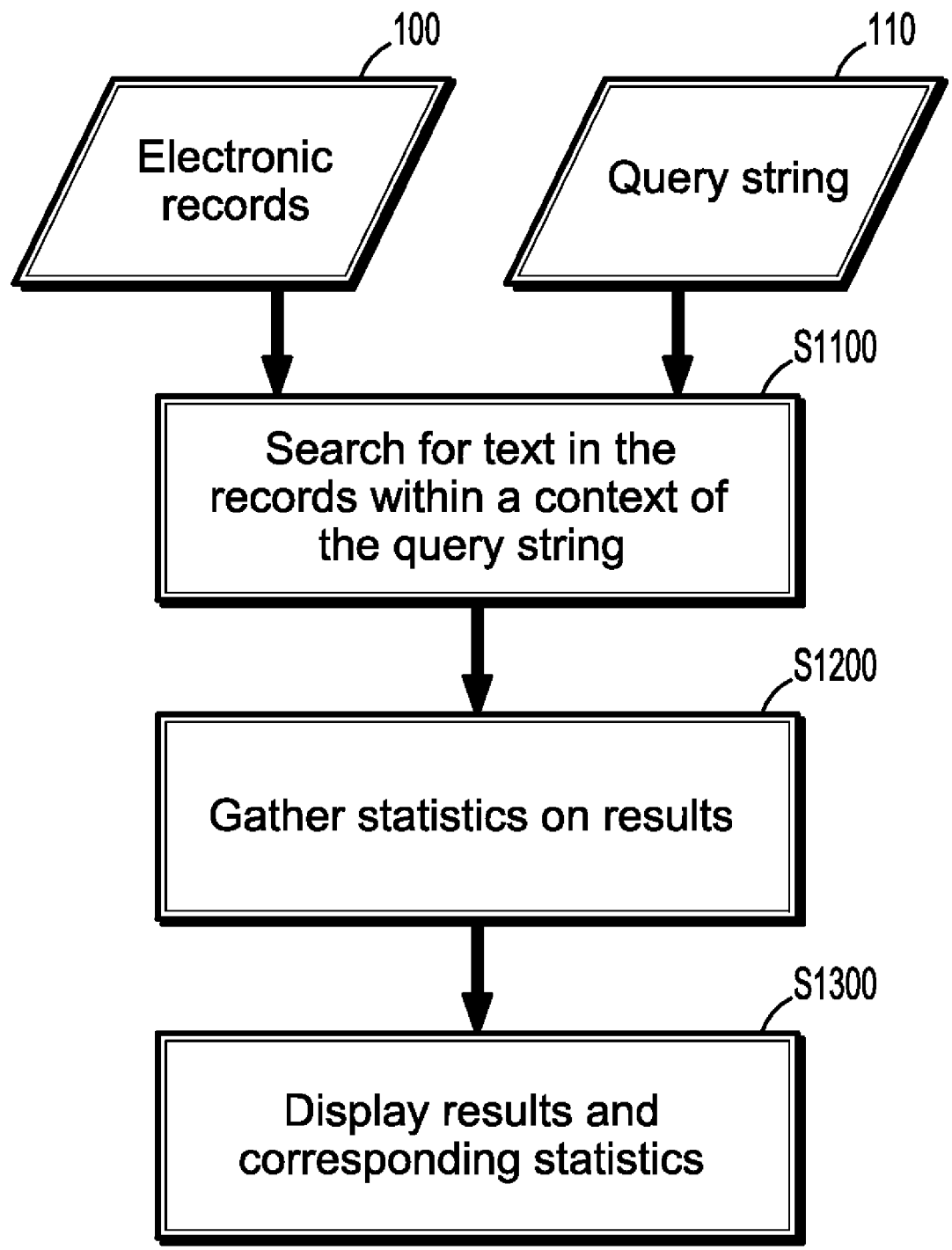
FIG. 10 illustrates a method of searching electronic records and displaying relevant data based on the search according to an exemplary embodiment of the present invention.

FIG. 10 illustrates a method of searching electronic records and displaying relevant data based on the search according to an exemplary embodiment of the present invention. The method includes the steps of searching for text in the electronic records within a context of an input query string (S1100), gathering statistics about the results (S1200), and displaying the results and the corresponding statistics (S1300). A context may include text that precedes or follows the entered query string in the electronic record that influences the meaning of the query string. The display of the results may list unique occurrences of the text in the electronic records and a corresponding count of their total occurrences in the records or a frequency of their occurrences.

It is to be understood that the particular exemplary embodiments disclosed above are illustrative only, as the invention may be modified and practiced in different but equivalent manners apparent to those skilled in the art having the benefit of the teachings herein. It is therefore evident that the particular exemplary embodiments disclosed herein may be altered or modified and all such variations are considered within the scope and spirit of the invention.

What is claimed is:

1. A system for searching one or more electronic records and displaying relevant data based on the search, the system comprising:
 a processor; and
 one or more non-transitory program storage devices readable by the processor, tangibly embodying a searching unit, a visual interface and a statistical analyzer executable by the processor,
  wherein the searching unit is configured to search for text in the one or more electronic records that are within a context of an entered query string, wherein the context is influenced by text that precedes or follows an instance of the entered query string in the one or more electronic records wherein a context type describes a structure in which the instance of the entered query string may be presented in the one or more electronic records, wherein the context type comprises at least a phrasal context, a bullet context, or a list context,
  wherein the statistical analyzer is configured to analyze results of the search, provide search statistics, and order the results associated with the entered query string based on the search statistics and the context of the entered query string, and
  wherein the visual interface is configured to display the search statistics and the results of the search presented in the structure corresponding to the context type.

2. The system of claim 1, wherein the text is determined to be within the context of the entered query string when it precedes or follows the instance of the entered query string up to a terminal character.

3. The system of claim 1, wherein the system is configured to search for strings in the one or more electronic records that are also within a context of a string related to the entered query string, wherein the related string is one of a synonym, hypernym, hyponym, inflection, or part of the query string.

4. The system of the claim 2, wherein the terminal character comprises one of punctuation, a bullet, or a space.

5. The system of claim 1, wherein the one or more electronic records comprise one of a medical, financial, or legal record.

6. The system of claim 1, wherein the system is further configured to suppress display of personal information of a patient from the results of the search.

7. The system of claim 1, wherein the statistics correspond to a frequency of occurrence for each of the results.

8. The system of claim 1, wherein the context type comprises a list context that returns a list as the results of the search.

9. The system of claim 1, wherein the searching unit is further configured to perform off-line indexing of text reports from multiple patient databases.

10. The system of claim 1, wherein the statistics relate to a type or institution of the electronic record.

11. The system of claim 1, wherein the searching unit is further configured to narrow its search based on one or more constraints relating to a medical record type or a medical institution.

12. The system of claim 1, wherein the system is further configured to filter the results of the search at different levels, wherein the levels include at least a patient level, a visit level, a physician/nurse level, or a patient group level.

13. The system of claim 1, wherein the system is further configured to derive logical rules from the results of the search to perform more refined data mining.

14. The system of claim 1, wherein the system is further configured to combine the results of the search based on co-occurrence statistics.

15. A method for searching one or more electronic records and displaying relevant data based on the search, the method comprising:

searching, by a computer, for text in the one or more electronic records that are within a context of an entered query string, wherein the context is influenced by text that precedes or follows an instance of the entered query string in the one or more electronic records, wherein a context type describes a structure in which the instance of the entered query string may be presented in the one or more electronic records, wherein the context type comprises at least a phrasal context, a bullet context, or a list context;

calculating, by the computer, search statistics based on results of the search and ordering the results associated with the entered query string based on the search statistics and the context of the entered query string; and displaying, by the computer, the search statistics and the results of the search presented in the structure corresponding to the context type.

16. The system of claim 15, wherein the text is determined to be within the context of the entered query string when it precedes or follows the instance of the entered query string up to a terminal character.

17. The method of claim 16, wherein the terminal character comprises one of punctuation, a bullet, or a space.

18. The method of claim 15, wherein the statistics correspond to a frequency of occurrence for each of the results.

19. The method of claim 15 further comprises suppressing display of personal information of a patient from the results of the search.

* * * * *